United States Patent
Bringley et al.

(10) Patent No.: US 9,862,813 B2
(45) Date of Patent: Jan. 9, 2018

(54) POROUS COMPOSITE FILLER COMPOSITIONS

(71) Applicant: Joseph Bringley, Rochester, NY (US)

(72) Inventors: Joseph F Bringley, Rochester, NY (US); Patrick M Lambert, Rochester, NY (US)

(*) Notice: Subject to any disclaimer, the term of this patent is extended or adjusted under 35 U.S.C. 154(b) by 17 days.

(21) Appl. No.: 14/915,639

(22) PCT Filed: Sep. 3, 2014

(86) PCT No.: PCT/US2014/053822
§ 371 (c)(1),
(2) Date: Feb. 29, 2016

(87) PCT Pub. No.: WO2015/034881
PCT Pub. Date: Mar. 12, 2015

(65) Prior Publication Data
US 2016/0222193 A1 Aug. 4, 2016

Related U.S. Application Data

(60) Provisional application No. 61/874,399, filed on Sep. 6, 2013.

(51) Int. Cl.
*A61K 6/083* (2006.01)
*C08L 67/00* (2006.01)
(Continued)

(52) U.S. Cl.
CPC .............. *C08K 9/04* (2013.01); *A61K 6/0005* (2013.01); *A61K 6/0008* (2013.01);
(Continued)

(58) Field of Classification Search
None
See application file for complete search history.

(56) References Cited

U.S. PATENT DOCUMENTS

| | | | | |
|---|---|---|---|---|
| 4,217,264 A * | 8/1980 | Mabie | ............... | A61K 6/083 106/35 |
| 4,306,913 A * | 12/1981 | Mabie | ............... | A61K 6/083 106/35 |

(Continued)

FOREIGN PATENT DOCUMENTS

| EP | 0983762 A1 * | 3/2000 | .......... A61K 6/0276 |
|---|---|---|---|
| EP | 0 983 762 | 8/2013 | |

(Continued)

OTHER PUBLICATIONS

International Search Report 2015034881A1.

*Primary Examiner* — Peter A Salamon
(74) *Attorney, Agent, or Firm* — Lynne M. Blank, Esq.

(57) ABSTRACT

The present invention relates to polymeric composites comprising inorganic fillers and organic, or organometallic, polymers. The filler compositions are used in the preparation of inorganic-organic polymeric composites, and, in particular, light curable composites. The composite fillers are used in dental applications, such as tooth restorations, for example, cavity fillings, adhesive compositions, veneers, crowns, bridges and teeth replacements. The inventive composition is a composite filler comprising porous inorganic particles having a diameter of 2-25 microns and a polymer occupying the pores of the porous inorganic particles, wherein the composite filler has a diameter of 2-25 microns.

20 Claims, 2 Drawing Sheets

(51) Int. Cl.
*C08K 9/04* (2006.01)
*A61K 6/00* (2006.01)
*A61K 6/02* (2006.01)
*A61K 6/027* (2006.01)
*C08L 33/14* (2006.01)

(52) U.S. Cl.
CPC ............ *A61K 6/0085* (2013.01); *A61K 6/024* (2013.01); *A61K 6/025* (2013.01); *A61K 6/027* (2013.01); *A61K 6/0235* (2013.01); *A61K 6/0245* (2013.01); *C08L 33/14* (2013.01)

(56) References Cited

U.S. PATENT DOCUMENTS

| | | | | |
|---|---|---|---|---|
| 4,503,169 | A | * | 3/1985 | Randklev ............... A61K 6/083 106/35 |
| 4,952,530 | A | * | 8/1990 | Brosnan ................. C03C 11/00 106/35 |
| 5,356,951 | A | * | 10/1994 | Yearn ..................... A61K 6/083 523/115 |
| 7,091,258 | B2 | | 8/2006 | Neubert |
| 8,617,306 | B2 | | 12/2013 | Lambert |
| 2011/0257292 | A1 | * | 10/2011 | Okubayashi ......... A61K 6/0005 523/115 |
| 2012/0004342 | A1 | * | 1/2012 | Lambert ............... C04B 14/041 523/115 |
| 2013/0005846 | A1 | * | 1/2013 | Yamazaki ........... A61K 6/0073 521/149 |

FOREIGN PATENT DOCUMENTS

| WO | WO2012/002996 | | 1/2012 | |
|---|---|---|---|---|
| WO | WO 2012002996 | A2 * | 1/2012 | ........... A61L 27/427 |

\* cited by examiner

POROUS COMPOSITE FILLER COMPOSITIONS

CROSS REFERENCE TO RELATED APPLICATIONS

This application is the national phase application of PCT/US2014/053822, entitled "POROUS COMPOSITE FILLER COMPOSITIONS" filed on Sep. 3, 2014 under 35 U.S.C. 371, which claims priority to U.S. Provisional Patent Application Ser. No. 61/874,399 by J. Bringley et al., entitled "POROUS COMPOSITE FILLER COMPOSITIONS", filed on Sep. 6, 2013, the disclosures of which are incorporated herein by reference.

FIELD OF THE INVENTION

The present invention relates to polymeric composites comprising inorganic fillers and organic, or organometallic, polymers. The invention relates to filler compositions that are used in the preparation of inorganic-organic polymeric composites, and, in particular, light curable composites. Still further, the invention relates to composite fillers that are used in dental applications, such as tooth restorations, for example, cavity fillings, adhesive compositions, veneers, crowns, bridges and teeth replacements.

BACKGROUND OF THE INVENTION

Inorganic-organic polymer composite materials are used in a wide variety of applications including structural materials, high performance composites, optical components, aerospace, biomedical implants and dental applications. Generally, composites are employed where performance requirements are demanding and not easily fulfilled with traditional structural materials. For example, inorganic materials, such as glass, ceramic and stone, are very hard, scratch resistant and even sometimes transparent (e.g., glass), but suffer from the fact that they are very heavy and brittle. Polymers, conversely, are light and durable, but have poor hardness, abrasion and wear resistance. Composites, made from the combination of inorganic materials and polymers, may have properties that lie in between, providing materials that are simultaneously strong but lightweight, hard but flexible, abrasion resistant and durable.

In order to achieve such properties, in practice, hard inorganic materials are mixed into polymers, or polymer precursors, monomers and/or oligomers, referred to as resins, and the mixture is then cured to form a composite. The inorganic materials are often referred to as fillers, although they may play the salient role in determining the properties of the composite. Glass or ceramic fillers are commonly used because they are low cost, and, more recently, nanomaterial fillers have been used to provide composites with performance advantages. Hereafter, inorganic addenda are referred to as performance additives.

Performance additives are an extremely important component of coatings and composite formulations. They impart a wide variety of properties to the end products including strength and toughness, scratch and mar resistance, UV absorption, optical properties, anticorrosion, and biocompatibility (for medical based coatings). Typical performance addenda are comprised of inorganic metal oxides, such as silica, titania, alumina, and zinc oxide; they may be categorized according to their size: micron-sized (0.2-100 μm) or nano-sized (1-200 nm).

There are several problems or difficulties generally experienced in mixing performance additives into polymers. First, polymers or polymer precursors may be viscous and the addition of performance materials only increases the viscosity and limits the loading of material that may be achieved, and creates difficulty in handling, molding and crafting the composite into an article of commerce. Second, inorganic performance materials generally have a high surface energy compared to resins, and the mismatch in the interfacial energy may cause the inorganic materials to agglomerate and/or aggregate, making a homogeneous dispersion difficult or impossible to achieve. This problem is particularly acute if the particle size of the performance additive is small, especially in the case of nanomaterials, i.e., materials with a particle size between about 1 to 200 nm.

The polymer industry is transforming from composites that are polymerized, or cured, using heat (thermal set polymers) to those that are cured using ultraviolet or visible light, or low energy electrons (UVEB). UVEB curable resins offer tremendous energy and waste savings to the coatings and composites industries because they are polymerized (cured) directly with light and also because they generally do not contain volatile diluents, such as solvents or carriers that may be considered hazardous air pollutants. UVEB curing is far more energy efficient, since it overcomes the thermal loss that is prevalent in conventional thermoset coating systems. Ironically, the fundamental advantages of UVEB systems, where a solventless medium is cured rapidly by radiation, are also the source of significant system limitations.

Light curing requires that the coating and/or object must be sufficiently transparent in the spectral region of curing, since the penetration depth and absorption of the curing radiation is essential to achieve rapid and efficient curing. This limits the performance additives (fillers, stabilizers, functional additives, and coating aids) that can be added to UVEB systems, since the additives must also fulfill the requirement of being optically transparent in the curing region of the spectrum. While there are some types of addenda that meet this requirement, their formulation into UVEB resins can be very difficult, since these systems do not contain diluents or volatile components.

Diluents (solvents and volatiles) act as dispersion aids and carriers that enable integration of a wide variety of functional additives into paints and coatings formulations. Diluents give the formulator tools with which to adjust viscosity and rheology, disperse solids and overcome formulation incompatibilities. These factors, in combination with the absorption requirements of UVEB formulations, greatly limit the performance additives that can be utilized.

The dental industry, primarily due to health concerns, is rapidly transitioning dental restoratives (e.g., cavity fillings, dental restorations) from the conventional mercury-based amalgams to highly filled, light curable, polymer-based composites. Polymer-based composites are safer and better match the color and appearance of human tooth enamel, but are often softer, not as strong or as durable as the traditional metal amalgams. To resolve these problems, manufacturers have developed microfilled polymer composites that have strength, hardness and durability close to that of the conventional amalgams. To achieve the performance requirements, polymers are highly filled at loadings of 70-80% by weight performance additives. It is generally desirable that the filling percentage be as high as possible to approximate the hardness of teeth, however, loadings greater than about 80% are difficult if not impossible to achieve.

From the patient's perspective, the aesthetic quality of the restoration is extremely important, since teeth are an important part of personal appearance. Matching the aesthetic quality of natural human enamel is difficult, since teeth, although opaque, have a translucent or opalescent quality that provides luster and visual brilliance. To achieve these qualities, some dental restorative manufacturers have developed performance additives that are closely matched in refractive index to the polymers used to prepare dental restoratives. The more closely index-matched the performance additives are to the polymer, the greater the translucency and aesthetic quality of the restoration. Because the two materials share the same index of refraction, there is little scatter of light and the resulting restorative composite resembles natural teeth in optical translucency and appearance. This also has the added benefit that it increases light penetration and the curing depth of the composite.

There are two types of fillers that are used in dentistry to give high optical translucency and aesthetic quality. The first is a glass or melt derived filler that is produced by melting a glass composition of known refractive index, rapidly cooling or quenching the melt, (for example into cold water) into a glass, and then pulverizing the glass to a given particle size, usually between about 0.4 and 10.0 microns. This process produces amorphous, shard-like particles of low surface area, usually between about 1-10 $m^2/g$. A prevalent example of this type of filler is barium glass.

The second is a microporous filler that is produced from the thermal treatment of mixtures of colloidal dispersions of oxides, such as silica, zirconia and alumina. The refractive index is controlled through control of the composition. This process was first developed by Mabie et al. U.S. Pat. Nos. 4,217,264 and 4,306,913, to produce amorphous, microporous mixed oxides of silica and zirconia, and later by Randklev U.S. Pat. No. 4,503,169 to produce crystalline, microporous mixed oxides of silica, zirconia, and other oxides.

The microporous fillers are highly fused materials consisting of silica and other oxide particles and, because they are processed at a temperature below the melting temperature of any of the components, they are porous and have a high surface area. As Randklev pointed out, the surface area may be as high as 200 $m^2/g$ and the average pore volume may be as high as 40% of the volume of the filler. These microporous fillers have received much attention because of their numerous advantages, including improved finish, gloss, strength, and abrasion resistance.

There is a problem, however, in that for microporous fillers, both the internal porosity and surface area is high, and it is difficult to achieve high loadings of the porous fillers in dental monomers. The internal pores soak up the organic resin, limiting the fraction of resin that may keep the suspension in a fluid state, and the viscosity rises exponentially making the paste unworkable.

There is an additional problem with modern dental composite restorations. Modern dental materials contain a liquid, polymerizable resin in the form of monomers, or monomer mixtures, as an essential component. It is known that, during polymerization, a volume contraction takes place. The volume contraction is often called shrinkage and is attributable to the development of covalent bonds between the monomer molecules during polymerization, whereby the distance between the molecules is decreased. During the preparation of pre-shaped parts, the polymerization shrinkage has a very disadvantageous effect on the dimensional stability and the mechanical properties of the molded bodies. In the case of adhesives and gluing compounds, the polymerization shrinkage adversely affects the adhesion properties and the bonding strength, which deteriorates the adhesion between restoration material and the natural tooth substance of dental materials. Voids and cracks may result which become reservoirs for bacteria and encourage the development of secondary caries.

In order to reduce the polymerization shrinkage of dental materials, the industry has developed pre-polymerized fillers in which a mixture of inorganic fillers and monomers is polymerized and then ground to the desired size and then mixed again with monomers to form a flowable mixture that can be molded in tooth restorations. Because a portion of the polymer is pre-polymerized, the amount of shrinkage is slightly reduced. The preparation and use of such fillers, sometimes called pre-polymers or composite fillers, has been described in the patent and scientific literature.

U.S. Pat. No. 5,356,951 to Yearn et al. discloses a composition for dental restorative material comprising: (a) a first methacrylate or acrylate monomer having at least one unsaturated double bond, (b) (i) a composite filler obtained by curing and pulverizing a mixture of a first glass powder component having a maximum particle diameter of 10 µm or less and a mean particle diameter of 0.1 to 5 µm with a second methacrylate or acrylate monomer having at least one unsaturated double bond, (ii) a second glass powder component having a maximum particle diameter of 10 µm or less and a mean particle diameter of 0.1 to 5 µm, and iii) a fine particle filler having a mean particle diameter of 0.01 to 0.04 µm, and a photo-polymerization initiator. The filler described is a non-porous filler.

U.S. Pat. No. 7,091,258 to Neubert et al. discloses a composition comprising: (i) 10 to 80 wt. % organic binder; (ii) 0.01 to 5 wt. % polymerization initiator; (iii) 20 to 90 wt. % particulate composite filler, comprising a polymerized mixture of organic binder and inorganic filler, the composite filler particles having an average particle size of 20 to 50 µm, each wt. % of (i), (ii), and (iii) relative to the total mass of the composition; and wherein the composition contains at most 10 wt. % composite filler particles having a size of <10 µm, relative to the total mass of the particulate composite filler in the composition. There is a problem, however, in that the material of Nuebert et al. requires extensive grinding in order to be used as a dental filler, and, at best, a relatively large particle size (20-50 µm) is achieved.

EP 0 983 762 A1 to Katsu discloses an organic-inorganic composite filler for use in dentistry. The composite filler is prepared by curing a mixture of a particulate filler with an average particle size of 20 nm or less and a methacrylate or acrylate monomer with a viscosity of 60 cP or more and pulverizing the cured mixture. The materials are said to be characterized by good polishability and good mechanical properties and have a smoothness and transparency corresponding to the natural tooth.

U.S. patent application Ser. No. 13/583,687 to Yamazaki et al. discloses an organic/inorganic composite filler that contains: inorganic agglomerated particles comprising agglomerations of inorganic primary particles having a mean diameter between 10 and 1000 nm; an organic resin phase that covers the surface of each inorganic primary particle and binds the inorganic primary particles to each other; and intra-agglomerate voids, formed between the organic resin phase covering the surface of each inorganic primary particle, with a pore volume (here, pore refers to holes with diameters between 1 and 500 nm) between 0.01 and 0.30 $cm^3/g$ as measured by mercury intrusion porosimetry. There is a problem, however, in that Yamazaki et al. is directed toward bonding or gluing together discreet primary particles with a polymer phase and does not provide high transparency filler materials.

Problem to be Solved

There is a problem in that the fillers of the prior art cannot meet all of the requirements of high strength, low surface area and high loading capacity, low shrinkage, high radiopacity, good wear and gloss, index matching for aesthetic properties, and the elimination of post-processing steps, such as grinding. There is a problem associated with the prior art in that the composite fillers are prepared with a relatively large amount of polymerized organic binder, usually in the range of 20-30 weight %. This limits the hardness and strength that can be achieved. There is a further problem in that the pre-polymerization essentially glues, or binds, the particles together into a mass that must then be pulverized and ground into a filler of smaller grain size. This step is time consuming and costly and further degrades the mechanical and aesthetic properties of the composites. Still further, it creates very small particles, often called fines, which increase the viscosity of the mixtures with monomers and limit the loading of the inorganic component. There is a further problem in that that the composite fillers contain air pockets or voids that degrade the optical and aesthetic properties of the fillers. There are additional problems in that the inorganic components of the composite fillers are not matched in refractive index with the organic portion, increasing the visual opacity and degrading the aesthetic quality of the restoration.

There is a need for fillers that may be used in dentistry to reduce shrinkage, that allow very high inorganic loading contents without causing a steep rise in viscosity. There is a need for fillers that do not require costly grinding procedures and that have adequate strength, hardness and aesthetic qualities. There is a need to provide technologies that allow for the facile dispersion of fillers into resins, which prevent aggregation and agglomeration and the buildup of viscosity in the composites, and allow for ease of handling, molding and fabrication. There is a need to provide performance additives to the UVEB industry that may be easily integrated and do not cause scattering or absorption of the curing light and limit the curing depth in UVEB coatings and composites. There is a need to produce fillers that can be loaded at high levels in dental monomers while maintaining acceptable viscosity.

SUMMARY OF THE INVENTION

The present invention includes several advantages, not all of which are incorporated in a single embodiment and describes a composite filler comprising porous inorganic particles having a diameter of 2-25 microns and a polymer occupying the pores of the porous inorganic particles, wherein the composite filler has a diameter of 2-25 microns.

Advantageous Effect of the Invention

The invention provides composite fillers that can be loaded at very high weight or volume fractions without negatively impacting viscosity, and that reduce the volume contraction or shrinkage of the composite. Surprisingly, composite fillers can be obtained that are index-matched to the monomers or resins into which they are placed, thereby increasing the transparency and aesthetic qualities of the composite. The infusion of polymers or pre-polymers into the porous inorganic particles can be used to adjust its refractive index and uniquely allows for preparation of fillers with very high radiopacity.

The invention also provides porous, mixed particle inorganic filler materials that are sintered together to form an extensive network of strong inorganic bonds, thus greatly improving filler strength. The mixed particles are sintered in a manner that leaves behind a matrix of open pores or channels into which monomers, oligomers and/or polymer precursors are infused. Once therein, the monomers, oligomers or pre-polymers are polymerized within the pores using light, heat or by chemical reaction to produce a composite filler. Surprisingly, the particles are not glued or bound together by the polymerization process, and the particle size before and after polymerization remains the same. The composite filler does not require pulverization or grinding and can be used directly in composite formulations.

DETAILED DESCRIPTION OF THE INVENTION

Figure 1:
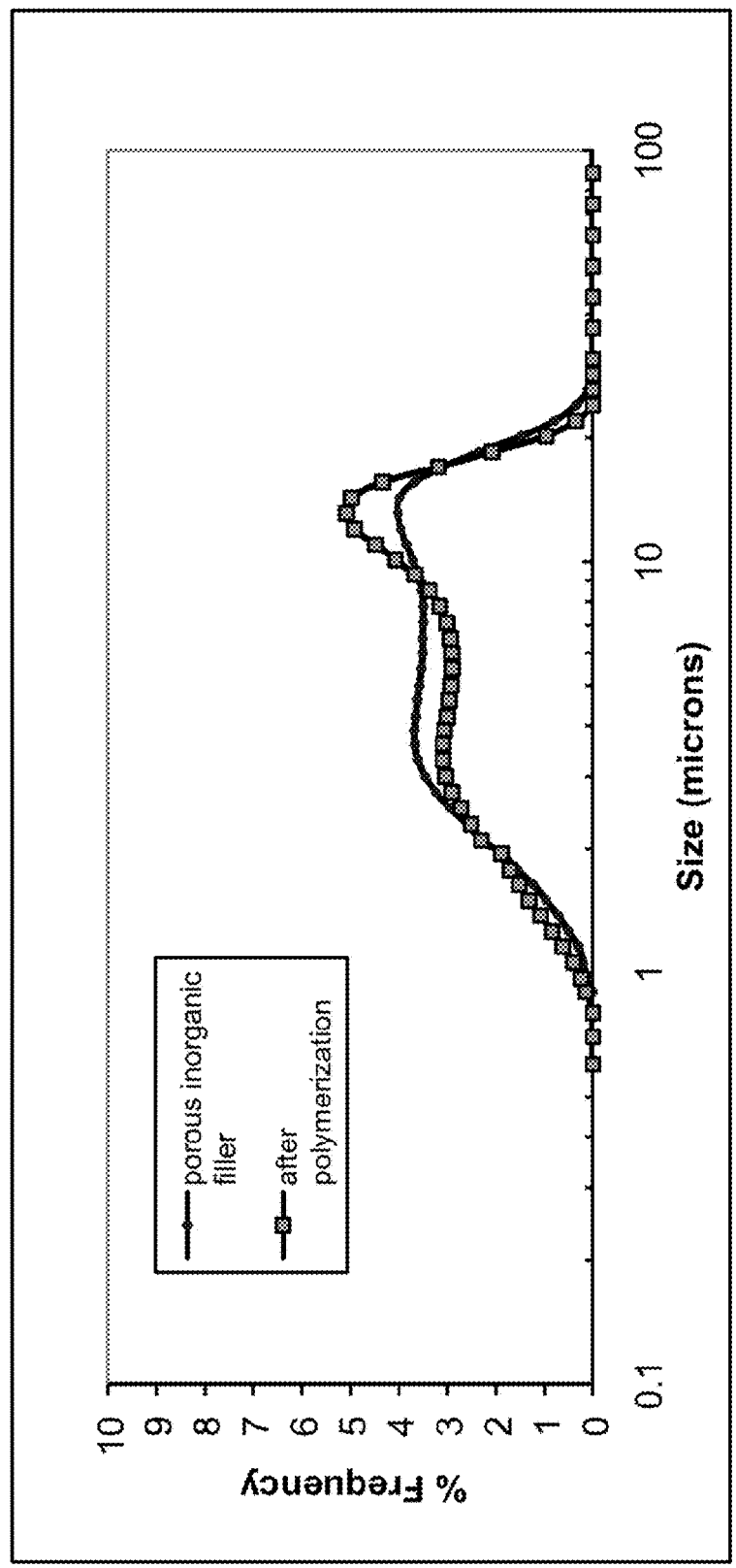
FIG. 1 represents the particle size distribution (in microns) of the porous inorganic filler and the composite filler (after polymerization) of Example 13.

The present invention relates to composite fillers comprising porous, inorganic fillers and organic, or organometallic, polymers. In particular, the invention relates to filler compositions that are used in the preparation of inorganic-organic polymeric composites, especially light curable composites. Still further, the invention relates to composite fillers that are used in dental applications, such as tooth restorations, for example, cavity fillings, adhesive compositions, veneers, crowns, bridges and tooth replacements. The composite fillers can also be used in coatings, moldings, optical composites, lightweight and high strength composites, and biomedical composites. The composite filler comprises open-pored inorganic particles having a diameter of 2-25 microns and a polymer occupies and substantially fills the open pores of the porous inorganic particles, wherein the composite filler has a diameter of 2-25 microns.

TERMS AND DEFINITIONS

Median particle diameter or median diameter, as used herein, refers to the volume-weighted, median particle diameter.

Heteroaggregate, as used herein, refers to a heterocoagulate that has been heated at a temperature sufficient to form strong chemical bonds between the distinct colloidal particles, fusing them together, usually a temperature of greater than 700° C.

Composite Filler, as used herein, refers to a filler comprising both and inorganic and organic portion.

Composite, as used herein, refers to a polymer that contains at least one inorganic filler, including a composite filler.

Resin, as used herein, refers to a polymerizable mixture of monomers, oligomers or other polymerizable molecules.

The inorganic particle materials of the invention are porous and contain micropores or microchannels that are substantially open. Porous inorganic filler materials for use in dentistry have been previously described by Mabie et al., U.S. Pat. Nos. 4,217,264 and 4,306,913 and Randklev, U.S. Pat. No. 4,503,169. They are typically produced by sintering the component oxides and/or non-oxides at high temperature (700-1100° C.). The sintering temperature is typically chosen such that it is below the melting temperature of any component of the mixture. Extensive melting of the components should be avoided since it may lead to particles that are non-porous. The preferred porous inorganic particles are mixed particles, or heteroaggregates, and comprise silica and at least one particle selected from the group consisting of alumina, zinc oxide, titania, zirconia, hafnia, yttria, rare earth oxides, boehmite, alkaline earth fluorides, calcium phosphates and hydroxyapatite. Heteroaggregates suitable for use in the invention are described in U.S. Pat. No. 8,617,306 to Lambert et al. and in Bringley et al. WO 2012/002996 A2, each incorporated herein by reference. More preferably the heteroaggregate comprises silica and at least one oxide selected from the group consisting of alumina, zinc oxide, titania, zirconia, yttria and rare earth oxides. These oxides are preferred because of their unique refractive indices and also because of their significant radiopacity. Also preferred are heteroaggregates comprising at least one oxide and a non-oxide filler selected from hydroxyapatite, fluoroapatite and alkaline earth fluorides. These non-oxide fillers are preferred because they contain calcium, phosphate and fluoride, all of which are known to promote dental health. Non-preferred materials are non-porous fillers such as those derived from melting process such as glasses, and discreet nanoparticle fillers that are substantially fully densified, although it is possible to use such materials as a minor component of the composite filler.

In a particular embodiment, it is preferred that the porous inorganic particles comprise at least one oxide selected from zirconia, yttria, and rare earth oxides at a concentration greater than 25%, and still more preferably greater than or equal to 30%, by weight. This is preferred because it greatly increases the radiopacity of the particles, a feature that is highly sought after for biomedical materials. As will be demonstrated, prior to this invention, such materials could be used only with difficulty in dentistry since the incorporation of large amounts of radiopaque components increased the refractive index of the filler outside of the range suitable for dentistry.

The porous inorganic particles have a diameter of 2-25 microns, more preferably from 3 to 20 microns and most preferably from 4 to 10 microns. These particle size ranges are preferred in dentistry because they produce composites that have good mechanical properties while also having good wear/abrasion and gloss properties.

The porous inorganic particle materials of the invention are most preferably produced by the heterocoagulation of colloids. The colloids used for preparing the porous inorganic particles of the invention are preferably selected from aqueous dispersible metal oxide particles including silica, alumina, zirconia, titania, zinc oxide, hafnia, yttria and rare earth oxides. Most preferably, the colloids are silica, alumina, titania, zirconia, or combinations thereof. Specific examples include colloidal, precipitated or fumed silica, aluminas, such as $Al_2O_3$ and its polymorphs, AlOOH (also known as boehmite), zirconia, $ZrO_2$ or hydrous zirconias, rare earth oxides, such as $Y_2O_3$ and $Yb_2O_3$, and the basic carbonates and nitrates of the aforementioned materials. It is possible to include also other metal oxides, finely ground glasses, and/or metal compounds, such as hydroxides, carbonates, halides, phosphates, nitrates, and the like. Preferred particles that are glasses include barium and strontium glasses although, as mentioned above, they should be used only as a minor component.

The preferred silica particles are colloidal, precipitated or fumed silicas having the general formula $SiO_2$. Silica is used in combination with a second colloid to produce a porous mixed oxide inorganic material. This is preferred, because it allows the refractive index of the composition to be modulated. Most preferred second colloids are colloids of alumina, zirconia, titania, alkaline earth fluorides, and hydroxyapatite.

It is preferred that the silica colloids have a particle size of less than 100 nm, and more preferably less than 50 nm, most preferably less than 25 nm. The other colloids of the invention have a particle size less than 50 nm, and preferably less than 25 nm, most preferably less than 10 nm. This is preferred, because colloids of these dimensions can be mixed to produce the mixed nanoparticle aggregates whose refractive index can be modulated predictably, based upon the index-weighted, volume fractions of the component nanoparticles.

The colloidal particles before heterocoagulation are preferably stable aqueous colloids. A stable aqueous colloid is one that does not settle or separate from aqueous dispersion for a period of at least one month or more. It is preferred that the stable aqueous colloids have a mean particle diameter of between about 1 and 100 nm, more preferably between 1 and 50 nm and most preferred between 1 and 25 nm.

The particle size of the sintered or infused particles of the invention may be characterized by a number of methods, or combination of methods, including coulter methods, light scattering methods, sedimentation methods, optical microscopy and electron microscopy. Light scattering methods sample a billion or more particles and are capable of giving excellent particle statistics. Light scattering methods may be used to give the percentage of particles existing within a given interval of diameter or size, for example, 90% of the particles are below a given value. Light scattering methods can be used to obtain information regarding mean particle size diameter, the median particle diameter, the mean number distribution of particles, the mean volume distribution of particles, standard deviation of the distribution(s) and the distribution width for the particles. In practice of the invention, it is preferred that the particle size is expressed as the median, volume-weighted particle size. This is the value (in microns) at which, by volume, half of the particles are larger and half are smaller.

The heterocoagulation may be accomplished by mixing the selected colloids and calcium or phosphorus sources, such as phosphates, in a suitable dispersion medium. The preferred dispersion medium is water. The mixing may be accomplished by using a suitable mixing apparatus, such as a blade or prop-like stirrer, a magnetic stirrer, a static mixer, in-line mixers, dispersators, or other high shear mixing apparatus. The mixing efficiency of the apparatus is dependent upon the type of mixing method chosen and the precise geometry and design of the mixer. Complete mixing of the two, or more solutions is preferably accomplished in less than about 10 seconds, and is more preferably accomplished substantially instantaneously.

After heterocoagulation of the particles, a porous inorganic material with a given refractive index is produced by drying and thermally processing to produce a sintered heteroaggregate. The drying and/or thermal processing may be accomplished in separate step, or combined into a single step. It is most preferred that the dried heterocoagulated mixed particles are thermally processed at a temperature below the melting point of the mixture, or at least below the melting point of the main component of the mixture. The thermal processing step increases the homogeneity of the mixture, decreases the apparent surface area, and importantly, increases the strength of the heteroaggregate. Generally, higher thermal processing temperatures provide stronger materials that have lower surface areas. However, there is a problem in that if the temperature is too high it may produce melted aggregates that may have poor abrasion and gloss properties when employed in composites. This is because the hard aggregates may pluck out from the surface of the composite leaving behind large voids. Alternatively, lower thermal processing temperatures lead to softer materials that have good gloss and abrasion, but poor strength. The precise thermal processing characteristics are therefore important to tune the properties of the composite. It is preferred that the thermal processing temperature is between about 700 to 1100° C., and more preferably from about 800-1000° C.

During the thermal processing step, the particle components fuse together to form strong, micron-sized heteroaggregates that consist of many millions of partially fused nanoparticles. This reduces the surface area of the particles and increases their strength. It is preferred that the heteroaggregates, after thermal processing, have a specific surface area between about 5-200 $m^2/g$ and it is more preferred that the surface area is controlled to be from about 10-100 $m^2/g$. It is still more preferred that the surface area is controlled to be from about 40-70 $m^2/g$. The reduction in surface area facilitates the integration of the compositions of the invention into polymers, monomers, composites and other formulations, and also increases the mechanical strength of the composites made therefrom. It is further important that the surface area is not reduced to below about 5 $m^2/g$, since low surface area materials have little porosity and limit the amount of polymer that can be infused within the pores.

After thermal processing, the porous inorganic particles contain crystalline and/or amorphous microdomains or regions. It is preferred that porous inorganic particles contain at least one crystalline or semicrystalline phase. It is also highly preferred that the crystalline or semicrystalline phases have microdomains less than about 50 nm and more preferably less than about 25 nm. The inclusion of such microdomains of crystalline or semicrystalline phases allows the refractive index of the porous inorganic particles to be tuned to a given value. The smaller the amorphous, crystalline or semicrystalline inclusions, the less scatter of visible light, which allows the refractive index to be tuned to a precise value. Materials of known and narrow refractive index dispersion are particularly useful in optical applications and in applications where the aesthetic quality of a device, item or article is prized. It is preferred that the refractive index of the porous inorganic particles is between about 1.46 and 1.60, most preferably from 1.54 to 1.58. Other useful ranges include from 1.48 to 1.58 and from 1.52 to 1.58. These ranges encompass the refractive index range for a wide variety of polymers and monomers that are useful in optical, medical and coating applications.

The porous inorganic particles of the invention are sintered to produce strong, micron-sized particles that are porous. It is preferred that the porosity is produced by high temperature thermal processing, and not by other methods that produce only relatively weak particles. The strength of the sintered particles of the invention is demonstrated by the fact that, regardless of the particle size of the colloids used in preparation, the porous inorganic particles are micron-sized and cannot be diminished back into primary particles, even with extensive milling or grinding. The porosity serves several functions including improving abrasion and wear resistance of the particles. Porous particles have improved abrasion and wear since they may shear particle by particle at the surface of a coating, whereas nonporous materials may pluck out leaving behind a void. The pores create internal surface, which may soak up monomer(s) by capillary force and exclude monomer from the external surfaces of the particle. The pores are substantially open and accessible by diffusion to small molecules and/or oligomers. It is preferred that the porous inorganic particles are substantially free of closed pores since closed pores are not accessible by diffusion and thus prevent polymerization within the pores, and because closed pores reduce transparency. It is preferred that the pores constitute approximately 10-70%, and more preferably 25-50% of the volume of the particle.

In the practice of the invention, an organic material, typically a pre-polymer, is infused within the pores of the porous inorganic material and polymerized therein to produce a composite filler. The pores are infused with monomers, oligomers and/or polymer precursors (collectively referred to as resins) that are subsequently polymerized within the pores, such that the pores are substantially filled with polymer. This leads to several advantages that have not been previously realized. First, it fills the pore volume so that the pores do not soak up resin when subsequently mixed within a resin, and thereby lowers the viscosity of the mixture and increases the loading capacity of the composite. Further, because the resin is polymerized substantially within the pores, it does not chemically bond or glue the porous inorganic nanoparticles into larger chunks that would then require milling or grinding to reduce the particle diameter. Still further, because the resin is polymerized within the pores, it does not contribute to volume contraction and shrinkage after it is mixed within a polymerizable resin and cured or polymerized. Finally, it has been discovered, surprisingly, that the index of refraction of the porous inorganic particles can be adjusted, or tuned, by proper selection of the polymerizable resin. This is highly significant because it allows for a precise matching of refractive index within the final composite, so that a composite or article with exceptional transparency can be produced. Still further, it uniquely allows for the design of fillers with both high radiopacity and high transparency.

It is preferred that the composite filler is at least 80 percent by weight, and more preferably greater than 84% by weight, porous inorganic particles. In practice of the invention it is important to match, as best as possible, the polymer volume with the pore volume. This insures that the majority of the resin, and after polymerization the polymer, is absorbed within the pores. Excessive polymer concentrations may lead to bonding or gluing of particles together, thus necessitating milling or grinding steps to diminish the particle size. Referring to FIG. 1, which depicts the particle size distribution of the porous inorganic particles (before infusion and polymerization), and the composite filler, it is observed that the particle size distribution is essentially unchanged after infusion and polymerization. It is preferred that the median particle diameter of the composite filler is not more than 2-times the median particle diameter of the porous inorganic particles. It is preferred that the composite filler has a median particle diameter between 2 and 25 microns, more preferably from 3 to 20 microns, and most preferably from 4 to 10 microns.

The composite filler of the invention has low surface area and therefore can be loaded at very high solids concentrations within resins. Resins containing the composite filler, when cured, produce composites with high strength, gloss, wear and abrasion characteristics, and low curing shrinkage. Most importantly, the composite filler, when properly matched to a resin system, and/or a cured resin system (i.e., a polymer), may produce composites that have exceptional aesthetic qualities such as high transparency and translucency.

The transparency of a composite or article can be measured in a variety ways, the most common of which is the fluid immersion method wherein a filler is dispersed within fluids of known refractive index and relative light transmission of the resulting dispersion is measured. The maximum light transmission corresponds to a matching of the refractive index between the filler and the fluid, and so provides a method for determining the refractive index of the filler. This provides the maximum transparency when, in practice, the composite fillers are dispersed within a resin and the resin cured to produce an article.

In a simple form, transparency refers to the ability to see through an object (such as the case for a window) and to recognize and discern objects on the other side. The transparency of articles prepared using the inventive compositions will be dependent upon the precise index match, the loading of the compositions within the resin, and the thickness of the article produced. Herein, the transparency is measured by way of a Transparency Index, described in the Description of Testing Materials: Optical Measurements in the Experimental section, wherein higher index indicates greater transparency. Transparency indices of 12 or greater indicate transparencies approaching window glass, whereas an index of about 8-11 represents a slightly scattering (translucent) medium, and indices of 7 and below indicate increasingly opaque materials. It is preferred that the transparency of the composite filler is greater than 8, it is more preferred that it is greater than 10.

An alternative method to measure transparency is by visible light transmission. In a preferred embodiment, it is preferred that the visible light transmission of a one centimeter thickness is greater than 25.0%, when the composite filler is dispersed into a fluid of substantially the same refractive index at a volume fraction of at least 25%. It is more preferred that the visible light transmission of a one centimeter thickness is greater than 50.0%, when the composite filler is dispersed into a fluid of substantially the same refractive index at a volume fraction of at least 25%. It is still more preferred that the visible light transmission is as high as possible.

In practice of the invention, it is most suitable to design composite fillers that are, as best as possible, matched in refractive index to the polymer matrix (meaning the cured resin) in which it is dispersed. Most light curable resin matrix systems have a refractive index between about 1.44 and 1.60, and their refractive index typically increases upon polymerization usually by about 0.02-0.03 units. It is preferred that the composite filler has a refractive index between 1.48 and 1.58, more preferably between 1.52 and 1.58.

The composite fillers of the invention are highly transparent and their refractive indices can be precisely tuned for a given application. This is especially advantageous because it allows for the design of composites whose refractive index can be precisely tuned to render articles with remarkable aesthetic and optical qualities. For the purpose of practicing the invention, it is essential to have a method for calculating (or estimating) the refractive index of a composite filler that is based upon its composition. The refractive indices of the composite fillers were calculated by using the volume-weighted average index of the components as described in the methods section. This is an accepted method for calculating the refractive index of mixtures. It is preferred that the difference between the measured (or determined) refractive index of the composite filler does not differ by more than 0.01 from the calculated volume average index of the composite filler.

In a particular embodiment of the invention, the refractive index of the composite filler may be adjusted, or tuned, by proper choice of resin. It has been discovered, surprisingly, that when the porous inorganic particles are infused with a polymer having a lower refractive index, the refractive index of the corresponding composite filler is reduced. Accordingly, when the porous inorganic particles are infused with a polymer having a higher refractive index, the refractive index of the corresponding composite filler is increased. Furthermore, the new refractive index can be predicted using the volume average refractive index. This is a surprising result since normally, refractive indices do not "average", and this may only occur if the components are dispersed homogeneously at a molecular or nanometer scale. When the components are larger than nanometer scale (above about 100 nm) scattering occurs yielding opacity, and the ability to adjust the index is diminished or lost.

The following explanation for this surprising result, although informative, does not limit the scope of the invention. The porous inorganic particles of the invention contain pores and channels that are essentially voids and generally filled with air. The air is essentially replaced by polymer during the infusion process. We believe the voids of the porous inorganic particles are very small, less than about 50 nm, and that the infused polymer is dispersed into the composite filler homogeneously, at nanometer scale. In this manner, because all components of the composite filler are present in microdomain sizes of less than about 50 nm, the new or adjusted refractive index is determined by the volume-weighted average of each of the components, and can be adequately described using the equation given in the Description of Testing Materials: Calculation of Refractive Indices in the Experimental section.

In the design of the composite fillers of the invention for medical purposes it is preferred that the radiopacity of the filler be as high as possible. Radiopacity allows for the imaging of implants using X-rays and therefore provides for diagnostic capabilities. For non-medical purposes, radiopacity is not necessary and it is more appropriate to exclude radiopaque materials since they are generally more expensive materials. However, for purposes of matching refractive index, non-radiopaque materials, such as silica, have a refractive index that is too low, whereas radiopaque materials such as zirconia have a refractive index that is too high. Thus mixed particle materials are used in order to achieve the desired refractive index.

Figure 2:
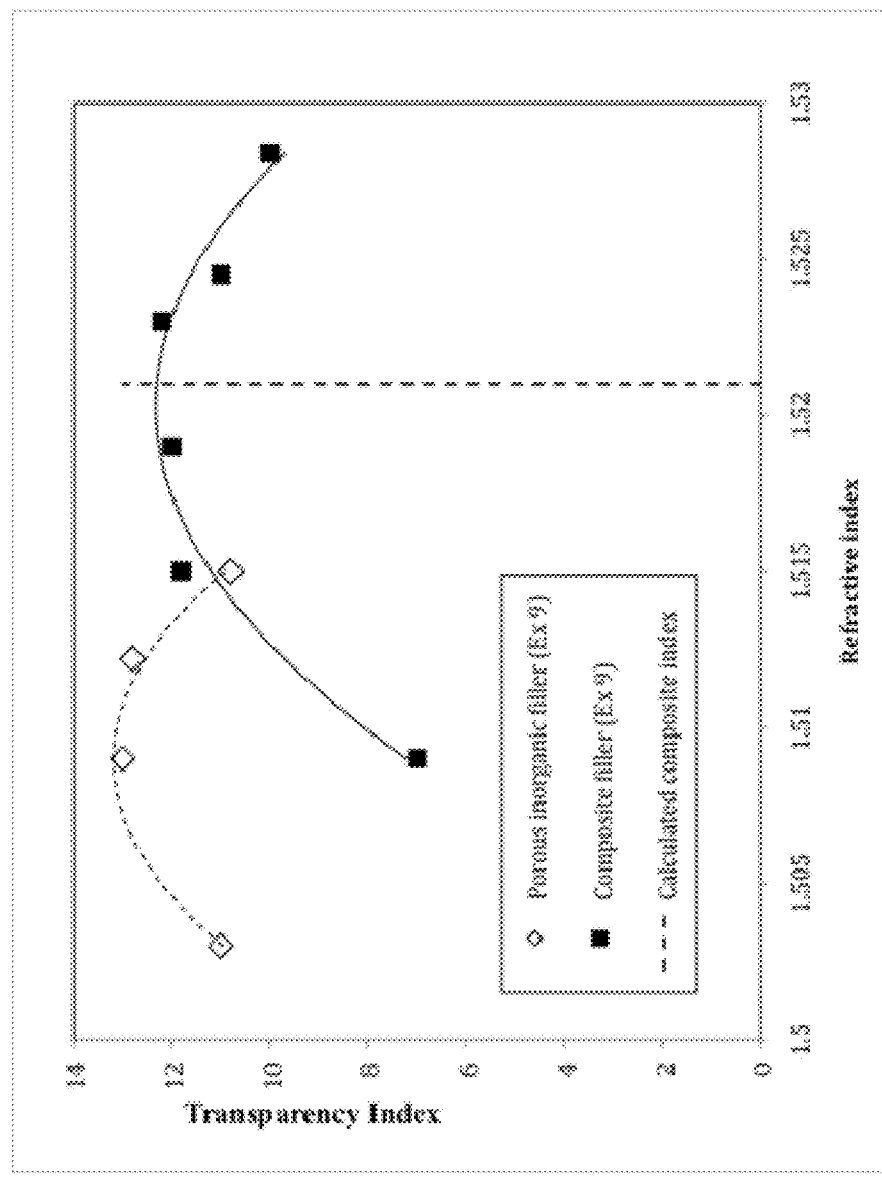
FIG. 2 represents the refractive index of the porous inorganic filler and the resulting composite filler of Example 9.

In dentistry, the most useful refractive index range for composites is from about 1.52 to 1.54. This corresponds to a zirconia concentration in the mixed particles of only about 20 to 25%. Thus, for purposes of achieving greater radiopacity there are limits to increasing zirconia concentration. By practice of the invention described herein, it is possible to increase significantly the zirconia concentration since the refractive index of the resulting porous inorganic may be too high, but can be adjusted back into the most useful range by selection of a polymer system whose refractive index is lower. Likewise, if the refractive index of the porous inorganic oxide is too low, it may be adjusted higher by selection of a polymer system whose refractive index is higher. FIG. 2 depicts the determined refractive indices of the porous inorganic particles (before infusion and polymerization), and the composite filler (after infusion and polymerization), and the calculated refractive index for the composite filler. It is observed that the refractive index of the composite filler is "adjusted" by practice of the invention, and that the degree of adjustment (i.e., the new refractive index) is adequately predicted by the method of calculation. For purposes of adjusting the refractive index, it is preferred that the difference between the refractive indices of the polymer and the porous inorganic particles is greater than 0.03, more preferably greater than 0.06.

In order to facilitate the integration of the compositions of the invention into polymers, monomers, composites or other formulations, it may be necessary to functionalize the surfaces of the porous inorganic particles with surface agents, for example, surfactants, coating aids, coupling agents, or the like. This step may be accomplished before, or after, the infusion and polymerization processes. It is preferred that it is done before the infusion and polymerization process. It is preferred that the particles have their surfaces functionalized by silane coupling agents, or hydrolyzed precursors of silane coupling agents having the general formula:

where a and b are integers from 1 to 3, (a+b) is less than or equal to 3, R and R' are organic groups having from 1-30 carbon atoms and R" is H, or an organic group having from 1 to 6 carbon atoms.

Alternatively, the silane coupling agent may have the general formula:

where a and R is as defined above and X is a halogen, Cl, Br or I.

Specific examples of silane coupling agents useful for practice of the invention include but are not limited to 3-mercaptopropyl(trimethoxy)silane, 3-mercaptopropylmethyl(diethoxy)silane, methacryloxypropyl(trimethoxy)silane, 2-[methoxy(polyethyleneoxy)propyl](trichloro)silane, 2-[methoxy(polyethyleneoxy)propyl](trimethoxy)silane, octyl(trimethoxy)silane, octadecyl(trimethoxy)silane, 3-isocyanatopropyldimethylchlorosilane, 3-isocyanatopropyl(triethoxy)silane, Bis(2-hydroxyethyl)-3-aminopropyltriethoxysilane, aminopropylsilanetriol, 3-aminopropyl(triethoxy)silane, 3-aminopropyl(trimethoxy)silane, N-(2-aminoethyl)-3-aminopropylsilanetriol, N-(2-aminoethyl)-3-aminopropyl(trimethoxy)silane, N-(2-aminoethyl)-3-aminopropylmethyldimethoxysilane, isopropyl(trimethoxy)silane, (3-glycidoxypropyl)methyldimethoxysilane, tetradecyldimethyl(3-trimethoxysilylpropyl)ammonium chloride, (3-trimethoxysilylpropyl)diethylenetriamine and octadecyldimethyl(3-ammonium)propyl(trimethoxy)silane.

To initiate the surface reaction, the particles and the surface agent(s) are mixed together in a high shear mixing zone within a dispersion medium. It is preferred that the dispersion medium is water, but other solvents or liquids may also be used.

In the preparation of the composite filler of the invention, the porous inorganic nanoparticle material is mixed with a resin or pre-polymer, usually within a solvent or medium in which the resin is soluble. Suitable media are any liquid in which the resin or pre-polymer is soluble, but preferred media are water and or organic solvent, such as acetone, methanol, ethanol, isopropanol, ether or other volatile organic solvents. A polymerization initiator and/or accelerator is then added to the mixture. Initiators and accelerates generally initiate polymerization only after a stimulus is applied such as heat, light or other radiation. After the mixture is homogeneously mixed, the solvent is then removed by vacuum distillation, or another evaporative process. This reduces the mixture to a free flowing powder.

The resin or pre-polymer portion of the powder is then polymerized by application of light, heat or other known means to initiate polymerization. It is preferred that the organic resin or pre-polymer material is polymerized substantially within the pores and not on the surface, or outside of, the porous inorganic nanoparticle material. Although some polymerization outside of the pores is difficult, if not impossible in practice to prevent, surprisingly, at the appropriate loadings, substantially all of the resin is polymerized within the pores.

In another embodiment of the invention, the composite filler particles of the invention are dispersed within a matrix. The matrix may comprise at least one fluid, polymer, oligomer, monomer or combinations thereof. It is preferred that the inventive compositions are dispersed within the polymer, oligomer, or monomer matrix at a loading of 1-80% by weight. It is preferred that the polymer, oligomer and/or monomer(s) are thermal or light curable. Useful examples of polymers for the matrix are acrylate-functional materials, methacrylate-functional materials, epoxy-functional materials, vinyl-functional materials, and mixtures thereof. Typically, the hardenable resin is made from one or more matrix forming oligomers, monomers, polymers, or blend thereof. Also useful are urethanes, fluoropolymers, siloxanes and latex polymers.

In certain embodiments, the inventive materials are used in dental applications or in orthopedic, or other in vivo, applications. It is preferred that the composite filler is a dental composite filler. It is preferred that the composite is dispersed in a light polymerizable resin matrix. In some embodiments it is preferred that that the refractive index of the light polymerizable resin matrix is essentially the same as the refractive index of the composite filler.

Polymerizable matrix materials suitable for use in these applications include hardenable organic materials having sufficient strength, hydrolytic stability, and nontoxicity to render them suitable for use in the oral or in vivo environment. Examples of such materials include acrylates, methacrylates, urethanes, carbamoylisocyanurates, epoxies, and mixtures and derivatives thereof. One class of preferred hardenable materials includes materials having polymerizable components with free radically active functional groups. Examples of such materials include monomers having one or more ethylenically unsaturated group, oligomers having one or more ethylenically unsaturated group, polymers having one or more ethylenically unsaturated group, and combinations thereof.

In the class of hardenable matrix resins having free radically active functional groups, suitable polymerizable components for use in the invention contain at least one ethylenically unsaturated bond, and are capable of undergoing addition polymerization. Such free radically ethylenically unsaturated compounds include, for example, mono-, di- or poly-(meth)acrylates (i.e., acrylates and methacrylates), such as, methyl (meth)acrylate, ethyl acrylate, isopropyl methacrylate, n-hexyl acrylate, stearyl acrylate, allyl acrylate, glycerol triacrylate, ethyleneglycol diacrylate, diethyleneglycol diacrylate, triethyleneglycol dimethacrylate, 1,3-propanediol di(meth)acrylate, trimethylolpropane triacrylate, 1,2,4-butanetriol trimethacrylate, 1,4-cyclohexanediol diacrylate, pentaerythritol tetra(meth)acrylate, sorbitol hexacrylate, tetrahydrofurfuryl (meth)acrylate, bis[1-(2-acryloxy)]-p-ethoxyphenyldimethylmethane, bis[1-(3-acryloxy-2-hydroxy)]-p-propoxyphenyldimethylmethane, ethoxylated bisphenol A di(meth)acrylate, and trishydroxyethyl-isocyanurate trimethacrylate; (meth)acrylamides (i.e., acrylamides and methacrylamides), such as (meth)acrylamide, methylene bis-(meth)acrylamide, and diacetone (meth)

acrylamide; urethane (meth)acrylates and the bis-(meth) acrylates of polyethylene glycols. Other suitable free radically polymerizable compounds include siloxane-functional (meth)acrylates and fluoropolymer functional (meth) acrylates. Mixtures of two or more free radically polymerizable compounds can be used, if desired.

Examples of other useful matrix polymers include natural and synthetic biopolymers, such as peptides, proteins, gelatin, poly(lactic acid), poly(glycolic acid), poly(caprolactone), chitosan and its derivatives, alginates and the like.

EXAMPLES

The following examples are provided to illustrate the invention.

Materials

All material concentrations are given as weight to weight percentages unless otherwise noted.

NALCO 2327® is a colloidal dispersion of silica in water, the mean silica particle diameter is 20 nm and the solids concentration 40.0%.

NALCO 2329® is a colloidal dispersion of silica in water, the mean silica particle diameter is 75-100 nm and the solids concentration 40.0%.

NALCO DVSN004® is a colloidal dispersion of silica in water, the mean silica particle diameter is 40 nm and the solids concentration 40.0%.

Dispal T25N4® is a trademarked product sold by Sasol America consisting of boehmite (AlOOH) with a mean primary particle diameter of about 6.5 nm and a dispersed particle size of about 40 nm.

Zirconyl Acetate® is a colloidal zirconia dispersion sold by Nyacol Nanotechnologies with a mean particle diameter of 5-10 nm.

Zirconia 50/14® is a colloidal zirconia dispersion sold by Nyacol Nanotechnologies with a mean particle diameter of 50 nm.

2,2'-Azobis(2-methylpropionitrile) (AIBN) is a thermal polymerization initiator purchased from Aldrich Chemical Company.

SR541, hexanediol diacrylate, Trimethylolpropane triacrylate, urethane dimethacrylate (UDMA), SR101 and triethylene glycol dimethacrylate (TEGDMA) are polymerizable methacrylate and acrylate monomers purchased from Sartomer USA, LLC.

Description of Testing Methods.

Calculation of Refractive Indices.

Refractive indices ($\eta_{tot}$) were estimated for all compositions using the relationship given in equation 1.

$$\eta_{tot}=(n_1V_1+n_2V_2+n_3V_3)/V_{tot} \quad (1)$$

where $\eta_1$, $\eta_2$ and $\eta_3$ are the refractive indices of the individual components and $V_1$, $V_2$ and $V_3$ are the respective volume fractions of that component. The refractive indices used were the reported values; (1.46 for $SiO_2$, 1.675 for gamma-$Al_2O_3$ and 2.115 for zirconia. The volumes for each phase are calculated based on the weight percentages and densities of the components. Monomer indices and densities were taken from the manufacturers published literature. For polymerized samples, the polymer index is estimated to increase by 0.025 units from that of the resin system; this increase is consistent with literature values of dental resins.

Optical Measurements.

The refractive index match and relative transparency in dental monomers was determined by making mixtures of the mixed oxide in a monomer of known refractive index at 35 wt. %. The monomers were purchased from Sartomer Chemical or Esstech Inc. and are methacrylate monomers commonly used in dental restoratives. The mixtures were sonicated to remove air bubbles, and 3.08 g of the mixtures were added into a glass vials to a depth of about 7.0 mm. The mixtures were placed on a light box and a series of optical targets were viewed by looking through the thickness of the sample. The mixtures were given a relative transparency score corresponding to the smallest font feature discernable (clearly visible and readable). Font sizes varied from 26-point to 2-point. For example, a rating of 1 indicates that only a 26-point font is readable, a score of 5 refers to readability of 18-point font or larger, 10=8-point and 13=2-point or larger. This simple qualitative method of determining transparency has an estimated accuracy of ±a score of 0.5. This method of ranking the relative transparency of the mixtures was validated using transmission spectrophotometry. The mixtures described above were measured on a Perkin Elmer Lambda 20 spectrometer at a thickness of 1.0 mm in a borosilicate glass slide cell (empty cell used as reference). Transparency was determined as the mean % transmission between 500 to 600 nm Samples were approximately 1 cm from the detector. Refractive indices of the powders were approximated by placing the powders in a series of fluids of known refractive index and noting the highest transparency.

Porous Filler A:

A porous inorganic filler consisting of silica and zirconia was prepared according to the following procedure: Into a 20 L reactor containing 2,076.1 g of zirconyl acetate (Nyacol Nanotechnologies, 20.0% zirconia solids) that was stirred with a prop-like mixer spinning at 2000 rpm, was added 4,104.6 g of colloidal silica (NALCO 2327; 40.0% silica solids) at a rate of 90.0 g/min After addition, the reaction mixture was allowed to stir for 1 hour. After preparation, the product was dried in a forced air oven at 110° C. The solid obtained was milled with 9 mm alumina beads for 16 hours and the resulting fine powder was fired in a programmable furnace at 960° C. for 2 hours and allowed to cool. The white powder obtained was then sieved through a 100 mm nylon screen to yield a fine white powder with a mean particle diameter of 3.1 mm.

Porous Filler B:

A porous inorganic filler consisting of silica and alumina was prepared according to the following procedure: An aqueous dispersion was prepared by the addition of 773.7 g of DISPAL T25N-80 to 16 L of distilled water with high shear mixing. After dispersion, the reaction vessel was stirred for an additional hour. Into the reaction vessel was then added 2003.5 g of NALCO 2327 dispersion (812 g of $SiO_2$) at a rate of 25.0 mL/min. The colloid was collected and dried at 100° C. to give a translucent solid. The solid was ball milled using 9 mm alumina beads to yield a fine powder. The powder was then loaded into fused silica crucibles and fired in a box furnace at 850° C. for 2 hours. The white powder obtained was then sieved through a 100 mm nylon screen to yield a fine white powder with a mean particle diameter of 17.4 mm.

Porous Filler C:

A porous inorganic filler consisting of silica and alumina was prepared according to the following procedure: An aqueous dispersion was prepared by the addition of 200.0 g of DISPAL T25N-80 to 1.0 L of distilled water with high shear mixing. After dispersion, the reaction vessel was stirred for an additional hour. Into the reaction vessel was then added 591.1 g of NALCO 2329 dispersion (240 g of $SiO_2$) at a rate of 25.0 mL/min. The colloid was collected and dried at 100° C. to give a translucent solid. The solid was ball milled using 9 mm alumina beads to yield a fine powder. The powder was then loaded into fused silica crucibles and fired in a box furnace at 850° C. for 2 hours. The white powder obtained was then sieved through a 100 mm nylon screen to yield a fine white powder with a mean particle diameter of 14.3 mm.

Non Porous Filler D:

A non-porous inorganic filler consisting of silica and alumina was prepared according to the following procedure: An aqueous dispersion was prepared by the addition of 1315.8 g of DISPAL T25N-80 (Sasol) to 9000 mL of distilled water with high shear mixing. After dispersion, the reaction vessel was stirred for an additional hour. Into the reaction vessel was then added 3654.6 g of NALCO 2329 dispersion (1500 g of $SiO_2$) at a rate of 45.0 mL/min. The colloid was collected and dried at 100° C. to give a translucent solid. The solid was ball milled using 9.5 mm alumina beads to yield a fine powder with a mean particle diameter of 7.4 mm. The powder was then loaded into fused silica crucibles and fired in a box furnace at 1075° C. for 3 hours. The resulting powder was then silanated as follows: to 1950 g of the fired powder above was added 3244 g isopropyl alcohol, 156 g of 3-methacryloxypropyl(trimethoxy) silane, 16.6 g of triethylamine and 53.0 g distilled water. The suspension was then roll milled using 3.0 mm zirconia beads to a particle size of 2.51 mm, the solvent removed under vacuum and then dried in an oven at 85° C.

Non Porous Glass Filler E:

Filler E is a commercial Barium glass filler purchased from Esstech, Inc. The reported mean particle diameter of this filler was 0.7 mm.

Non Porous Glass Filler F:

Filler F is a commercial Barium glass filler purchased from Schott Glass. The reported mean particle diameter of this filler was 0.4 mm.

Non Porous Filler G:

Filler G is a commercial silica colloid purchased from Nissan Chemical and sold under the trade name IPA-ST-ZL. It is a 30.0 weight % colloidal suspension of silica in isopropanol, the mean particle diameter of the silica is 100 nm.

Non Porous Filler H:

Filler H is a spherical silica-zirconia filler made by a sol gel method having a primary particle size of 200 nm.

Infusing of Porous Fillers with Thermal Polymerization.

Comparison Example 1

Filler A (above), was silanated with gamma-methacrloxypropyl(trimethoxy)silane as follows: 25.0 g of the filler was placed into a round bottom flask along with 30.0 g of acetone, 2.25 g gamma-methacrloxypropyl(trimethoxy)silane and 0.50 g 0.1 N acetic acid and stirred for 4 hours at 45-50° C. and the solvent removed by evaporation under vacuum. The sample was then heated at 110° C. for 4 hours under nitrogen. This procedure yielded a white powder that contained 0.0% polymer by weight.

Example 1

This example was performed identically to comparison example 1 except that after stirring for 4 hours at 45-50° C., 2.50 g of SR541 monomer and 25.0 mg of AIBN was added just prior to solvent removal. This procedure yielded a white powder that contained 9.1% polymer by weight.

Example 2

This example was performed identically to comparison example 1 except that after stirring for 4 hours at 45-50° C., 5.00 g of SR541 monomer and 50.0 mg of AIBN was added just prior to solvent removal. This procedure yielded a white powder that contained 16.7% polymer by weight.

Comparison Example 2

This example was performed identically to comparison example 1 except that after stirring for 4 hours at 45-50° C., 8.33 g of SR541 monomer and 81.0 mg of AIBN was added just prior to solvent removal. This procedure yielded a white powder that contained 25.0% polymer by weight, the powder was gritty and difficult to disperse back into SR541 monomer.

Comparison Example 3

This example was performed identically to comparison example 1 except that after stirring for 4 hours at 45-50° C., 10.0 g of SR541 monomer and 100.0 mg of AIBN was added just prior to solvent removal. This procedure yielded a white powder that contained 28.6% polymer by weight, the powder was gritty and could not be dispersed back into back into SR541 monomer.

Comparison Example 4

This example was performed identically to comparison example 1 except that after stirring for 4 hours at 45-50° C., 12.5 g of SR541 monomer and 125.0 mg of AIBN was added just prior to solvent removal. This procedure yielded a polymerized mass that contained 33.0% polymer by weight.

Comparison Example 5

This example was performed identically to comparison example 1 except that after stirring for 4 hours at 45-50° C., 25.0 g of SR541 monomer and 250.0 mg of AIBN was added just prior to solvent removal. This procedure yielded a polymerized mass that contained 50.0% polymer by weight.

TABLE 1

Examples 1 and 2 and Comparison Examples.

| Example or Comp. Example | Filler | % Monomer | Particle size d(50) before polymerization | Particle size d(50) after polymerization | Transparency Index | Viscosity at 60.0% solids in Monomer |
|---|---|---|---|---|---|---|
| C1 | A | none | 3.14 | 3.11 | 11.5 | high viscosity gel |
| 1 | A | 9.1 | 2.78 | 2.84 | 12 | flowable liquid |
| 2 | A | 16.7 | 2.74 | 2.69 | 12 | flowable liquid |
| C2 | A | 25 | 2.6 | >100 | 12 | flowable liquid |
| C3 | A | 28.6 | 2.52 | >100 | 12 | Not dispersible |
| C4 | A | 33 | 3 | polymerized mass | nm | nm |
| C5 | A | 50 | 3 | polymerized mass | nm | nm |

The data of Table 1 show that, surprisingly, the addition of monomer to a porous filler followed by its thermal polymerization does not increase the median particle size diameter, if the monomer loading is less than about 25% by weight. This is presumably because the monomer is absorbed into the pores of the filler and is polymerized therein. At loadings above about 25.0 wt. % monomer, the pores are essentially filled and polymerization glues the particles together, resulting in large chunk like particles or a polymerized mass that must be pulverized. The data of Table 1 also show that the transparency index of the filler is high, indicating an excellent refractive index match of the infused filler and monomer. The inventive examples of Table 1 show good dispersability and low viscosity in monomer.

Infusing of Porous Fillers with Light-Induced Polymerization.

RESIN A was a light-polymerizable monomer mixture comprising 50 weight percent SR541, 30 weight % ethoxylated bis-GMA, 15 weight percent UDMA and 5 weight percent TEGDMA. Into this mixture was then dissolved 0.5 weight percent camphorquinone and 0.7 weight percent 4-dimethylaminobenzoic acid as the initiator and accelerator, respectively.

Comparison Example 6

Filler A (above), was silanated with gamma-methacrloxypropyl(trimethoxy)silane as follows: 25.0 g of the filler was placed into a round bottom flask along with 30.0 g acetone, 2.25 g gamma-methacrloxypropyl(trimethoxy)silane and 0.50 g 0.1 N acetic acid and stirred for 96 hours at 25° C. and the solvent removed by evaporation under vacuum. The sample was then light cured in air using a dental curing light (Dentsply, model QHL75) with 100 seconds exposure at a distance of 1.0 cm. This procedure yielded a silanated white powder that contained 0.0% polymer by weight.

Example 3

This example was performed identically to comparison example 6 except that after stirring for 96 hours at 25° C., 2.03 g of RESIN A was added just prior to solvent removal. The sample was then light cured in air using a dental curing light (Dentsply, model QHL75) with 100 seconds exposure at a distance of 1.0 cm. This procedure yielded a silanated white powder that contained 7.5% polymer by weight.

Example 4

This example was performed identically to comparison example 6 except that after stirring for 96 hours at 25° C., 2.78 g of RESIN A was added just prior to solvent removal. The sample was then light cured in air using a dental curing light (Dentsply, model QHL75) with 100 seconds exposure at a distance of 1.0 cm. This procedure yielded a silanated white powder that contained 10.0% polymer by weight.

Example 5

This example was performed identically to comparison example 6 except that after stirring for 96 hours at 25° C., 3.57 g of RESIN A was added just prior to solvent removal. The sample was then light cured in air using a dental curing light (Dentsply, model QHL75) with 100 seconds exposure at a distance of 1.0 cm. This procedure yielded a silanated white powder that contained 12.5% polymer weight.

TABLE 2

| Example or Comp. Example | Filler | % light curable resin A | Particle size d(50) before polymerization | Particle size d(50) after polymerization | Transparency Index | Viscosity at 60.0% solids in Monomer |
|---|---|---|---|---|---|---|
| C6 | A | none | 3.04 | 3.24 | 12 | not dispersible |
| 3 | A | 7.5 | 2.97 | 2.96 | 12 | low viscosity gel |
| 4 | A | 10 | 3.27 | 2.95 | 12 | flowable liquid |
| 5 | A | 12.5 | 3.1 | 2.95 | 12 | flowable liquid |

The data of Table 2 show that that, surprisingly, the addition of a light curable resin to a porous filler followed by its radiation induced polymerization does not increase the median particle diameter. This is again presumably because the monomer is absorbed into the pores of the filler and is polymerized therein. The data of Table 1 also show that the transparency index of the filler is not affected by the polymer infusion but that the viscosity characteristics are greatly improved.

Infusing of Porous and Nonporous Fillers.

RESIN B was a thermal polymerizable monomer mixture comprising 60 weight percent SR541, 20 weight percent hexanediol diacrylate, and 20 weight percent Trimethylolpropane triacrylate.

Example 6

20.0 g of porous Filler B, 25.0 g acetone, 1.20 g of gamma-methacrloxypropyl(trimethoxy) silane and 0.50 g 0.1 N acetic acid were stirred together in a 250 mL round bottom flask for 24 hours. After this time, was then added 3.3 g of resin B and 0.40 g of a 10% solution of AIBN. The solvent was then removed at 35° C. under vacuum. The dried powder was then placed in a vacuum oven at 105° C. for 4 hours in a nitrogen atmosphere to induce polymerization.

Example 7

20.0 g of porous Filler C, 25.0 g acetone, 1.20 g of gamma-methacrloxypropyl(trimethoxy) silane and 0.50 g 0.1 N acetic acid were stirred together in a 250 mL round bottom flask for 24 hours. After this time, was then added 3.3 g of resin B and 0.40 g of a 10% solution of AIBN. The solvent was then removed at 35° C. under vacuum. The dried powder was then placed in a vacuum oven at 105° C. for 4 hours in a nitrogen atmosphere to induce polymerization.

Comparison Example 7

Comparison Example 7 was performed in an identical manner as that of Example 6, except that 20.0 g of nonporous Filler D was used to replace Filler B.

Comparison Example 8

Comparison Example 8 was performed in an identical manner as that of Example 6, except that 20.0 g of nonporous Filler E was used to replace Filler B.

Comparison Example 9

Comparison Example 9 was performed in an identical manner as that of Example 6, except that 20.0 g of nonporous Filler F was used to replace Filler B.

Comparison Example 10

Comparison Example 10 was performed in an identical manner as that of Example 6, except that 20.0 g of nonporous Filler G was used to replace Filler B.

TABLE 3

| Example or Comp. Example | Filler (Type) | Weight % Resin | Mean particle diameter d(50) before polymerization (microns) | Mean particle diameter d(50) after polymerization (microns) | Sieve Yield through 100 micron sieve |
|---|---|---|---|---|---|
| 6 | B (porous) | 14.2 | 14.2 | 9.3 | 100% |
| 7 | C (porous) | 14.2 | 14.2 | 8.8 | 100% |
| C7 | D (nonporous) | 14.2 | 2.51 | 20.9 | 60% |
| C8 | E (nonporous) | 14.2 | 0.7 | 23.3 | 30% |
| C9 | F (nonporous) | 14.2 | 0.4 | 12.4 | 30% |
| C10 | G (nonporous) | 14.2 | 0.1 | >100 | 19% |

The data shown in Table 3 show that the porous inorganic fillers of the invention can be infused with polymerizable resin, and the resin is polymerized within the intrinsic pores of the filler without gluing the particles together. In comparison, polymerization of resin around nonporous materials only serves to solidify or glue the particles into a continuous mass, or in the best case, yields a particle size that is large (above about 10 and unsuitable for many applications. Adjustment of Refractive Index.

Example 8

A porous inorganic filler consisting of silica and zirconia was prepared according to the following procedure. Into a 1 L reactor containing 342.2 g of zirconyl acetate (Nyacol Nanotechnologies, 20.6% zirconia solids) that was stirred with a prop-like mixer spinning at 2000 rpm, was added 438.0 g of colloidal silica (NALCO 2327; 40.9% silica solids) at a rate of 25.0 g/min After addition, the reaction mixture was allowed to stir for 1 hour. After preparation, the product was dried in a forced air oven at 110° C. The solid obtained was milled with 9 mm alumina beads for 10 hours and the resulting fine powder was fired in a programmable furnace at 960° C. for 2 hours and allowed to cool. The white powder obtained was then sieved through a 100 µm nylon screen to yield a fine white powder with a median particle diameter of 6.45 and a refractive index of 1.546. This powder was infused with triethyleneglycol dimethacrylate (refractive index=1.458) using the following procedure. 40.0 g of the porous inorganic filler was suspended in 40.0 g of isopropyl alcohol, 2.4 g of gamma-methacryloxypropyl (trimethoxy) silane and 0.70 g 0.1 N acetic acid. The mixture was then agitated for 20 hours. To this mixture was then added 6.60 g of the monomer, the solvent was removed on a rotary evaporator and the powder was polymerized under nitrogen for 3 hours at 105° C. The composite filler was a white powder with a median particle diameter of 6.68 This example represents the adjustment of the refractive index of a porous inorganic particle by infusion to achieve a calculated target/aim refractive index. Data are shown in Table 4.

Example 9

A porous inorganic filler consisting of silica and zirconia was prepared according to the following procedure: Into a 4 L reactor containing 1364.3 g of zirconyl acetate (Nyacol Nanotechnologies, 20.6% zirconia solids) that was stirred with a prop-like mixer spinning at 2000 rpm, was added 3219.5 g of colloidal silica (NALCO 2327; 40.9% silica solids) at a rate of 50.0 g/min After addition, the reaction mixture was allowed to stir for 1 hour. After preparation, the product was dried in a forced air oven at 110° C., the solid obtained was milled with 9 mm alumina beads for 2 hours and the resulting fine powder was fired in a programmable furnace at 960° C. for 2 hours and allowed to cool. The white powder obtained was then sieved through a 100 µm nylon screen to yield a fine white powder with a median particle diameter of 8.17 and a refractive index of 1.510. This powder was infused with ethoxylated bisphenol A dimethacrylate (SR101, Sartomer Chemical, (refractive index= 1.542)) as described in Example 8. The composite filler was a white powder with a median particle diameter of 8.7 Data are shown in Table 4 and illustrated by FIG. 2.

Example 10

A porous inorganic filler consisting of silica and zirconia was prepared according to the following procedure: Into a 8 L reactor containing 1702.1 g of zirconyl acetate (Nyacol Nanotechnologies, 20.7% zirconia solids) that was stirred with a prop-like mixer spinning at 2000 rpm, was added 4089.3 g of colloidal silica (NALCO DVSZN004; 40.3% silica solids) at a rate of 35.0 g/min. After addition, the reaction mixture was allowed to stir for 1 hour. After preparation, the product was dried in a forced air oven at 110° C., the solid obtained was milled with 9 mm alumina beads for 4 hours and the resulting fine powder was fired in a programmable furnace at 985° C. for 2 hours and allowed to cool. The white powder obtained was then sieved through a 100 µm nylon screen to yield a fine white powder with a median particle diameter of 6.29 µm, and a refractive index of 1.510. This powder was infused with ethoxylated bisphenol A dimethacrylate (SR101, Sartomer Chemical, (refractive index=1.542)) as described in Example 8. The composite filler was a white powder with a median particle diameter of 5.8 µm. Data are shown in Table 4.

Example 11

A porous inorganic filler consisting of silica and zirconia was prepared according to the following procedure: Into a 2 L reactor containing 255.8 g of zirconyl acetate (Nyacol Nanotechnologies, 20.6% zirconia solids) that was stirred with a prop-like mixer spinning at 2000 rpm, was added 610.1 g of colloidal silica (NALCO 2329; 40.5% silica solids) at a rate of 25.0 g/min After addition, the reaction mixture was allowed to stir for 1 hour. After preparation, the product was dried in a forced air oven at 110° C., the solid obtained was milled with 9 mm alumina beads for 6 hours and the resulting fine powder was fired in a programmable furnace at 950° C. for 2 hours and allowed to cool. The white powder obtained was then sieved through a 100 µm nylon screen to yield a fine white powder with a median particle diameter of 6.82 µm, and a refractive index of 1.510. This powder was infused with ethoxylated bisphenol A dimethacrylate (SR101, Sartomer Chemical, (refractive index=1.542)) as described in Example 8. The composite filler was a white powder with a median particle diameter of 5.9 μm. Data are shown in Table 4.

Example 12

A porous inorganic filler consisting of silica and zirconia was prepared according to the following procedure: Into a 4 L reactor containing 799.4 g of zirconyl acetate (Nyacol Nanotechnologies, 20.6% zirconia solids) that was stirred with a prop-like mixer spinning at 2000 rpm, was added 940.2 g of colloidal silica (NALCO 2327; 40.9% silica solids) at a rate of 35.0 g/min After addition, the reaction mixture was allowed to stir for 1 hour. After preparation, the product was dried in a forced air oven at 110° C., the solid obtained was milled with 9 mm alumina beads for 19 hours and the resulting fine powder was fired in a programmable furnace at 960° C. for 3 hours and allowed to cool. The white powder obtained was then sieved through a 100 μm nylon screen to yield a fine white powder with a median particle diameter of 3.8 μm, and a refractive index of 1.553. This powder was infused with triethyleneglycol dimethacrylate (refractive index=1.458) as described in Example 8. The composite filler was a white powder with a median particle diameter of 8.7 μm. Data are shown in Table 4.

Comparison Example 11 nonporous Filler H was infused with a mixture of SR541 and TEGDMA (60:40) (refractive index=1.50) as described in Example 6 and polymerized under nitrogen for 3 hours at 105° C. The final infused composite was a white powder with a median particle diameter of 96.1 μm. Data are shown in Table 4.

Comparison Example 12 nonporous Filler H was infused with triethyleneglycol dimethacrylate (refractive index=1.458) as described in Example 6 and polymerized under nitrogen for 3 hours at 105° C. The final infused composite was a white powder with a median particle diameter of 82.1 μm. Data are shown in Table 4.

TABLE 4

| Example or Comp. Example | Silica particle size (nm) | Refractive Index | Transparency score of porous filler at refractive index | Calculated refractive index (aim) after infusion | Transparency score at aim refractive index after infusion |
|---|---|---|---|---|---|
| 8 | 20 | 1.546 | 13 | 1.524 | 12 |
| 9 | 20 | 1.510 | 13 | 1.521 | 12 |
| 10 | 40 | 1.510 | 13 | 1.521 | 11 |
| 11 | 90 | 1.510 | 13 | 1.521 | 10 |
| 12 | 20 | 1.553 | 11.5 | 1.528 | 12 |
| C11 | 200 | 1.535 | 5 | 1.523 | 2.5 |
| C12 | 200 | 1.535 | 5 | 1.514 | 2 |

The data of Table 4 show that it is possible to move or adjust the refractive index of a porous inorganic filler thorough selection of a given resin. Examples 9, 10 and 11 show that for a filler of refractive index 1.510, it is possible to increase the refractive index while still maintaining high transparency. Examples 8 and 12 show that the index of a high refractive index filler (i.e., 1.546) can be moved or adjusted lower by infusion of an appropriate monomer (TEGDMA, n=1.458); the data also show that the porous inorganic fillers with small primary particles size show better conservation of transparency and therefore are preferred. Moreover, the data of Table 4 show that it is possible to adjust high refractive index porous fillers into a range that is most suitable for dentistry (from about 1.52-1.54). This is significant because it allows for the preparation of fillers that are highly radiopaque. Hitherto this discovery, such materials were not possible since zirconia, yttria and rare earth oxides have high refractive induces (above about 2.0) and could only be used in small amounts for aesthetic dentistry.

Example 13

A porous inorganic filler consisting of silica and zirconia was prepared according to the following procedure: Into a 20 L reactor containing 4166.7 g of zirconyl acetate (Nyacol Nanotechnologies, 20.64% zirconia solids) that was stirred with a prop-like mixer spinning at 2000 rpm. was added 7667.9 g of colloidal silica (NALCO 2327; 40.95% silica solids) at a rate of 300.0 g/min After addition, the reaction mixture was allowed to stir for 1 hour. After preparation, the product was dried in a forced air oven at 110° C., the solid obtained was milled with 9 mm alumina beads for 3 hours and the resulting fine powder was fired in a programmable furnace at 960° C. for 3 hours and allowed to cool. The white powder obtained was then sieved through a 100 μm nylon screen to yield a porous inorganic filler with a median particle diameter of 5.9 μm. To 3,000 g of the porous inorganic filler was added 3,000 grams acetone, 180.0 g gamma-methacryloxypropyl(trimethoxy) silane and 54.0 g 0.1 N acetic acid. The mixture was then agitated for 20 hours. To this mixture was then added 495.0 g of RESIN B, the solvent was removed on a rotary evaporator and the powder was polymerized under nitrogen for 5 hours at 105° C. The final infused composite filler was a white powder with a median particle diameter of 6.79 This example demonstrates that the size of the porous inorganic particle does not change by infusion. The original size of the porous inorganic particle is essentially the same as the composite filler. This is illustrated in FIG. 1.

The invention has been described in detail with particular reference to certain preferred embodiments thereof, but it will be understood that variations and modifications can be effected within the spirit and scope of the invention.

The invention claimed is:

1. A composite filler comprising porous inorganic particles having a diameter of 2-25 microns and a polymer occupying the pores of the porous inorganic particles, wherein the composite filler has a diameter of 2-25 microns before and after polymerization.

2. The composite filler of claim 1, wherein the porous inorganic particles comprises particles of silica and at least one particle selected from the group consisting of alumina, zinc oxide, titania, zirconia, hafnia, yttria, rare earth oxides, boehmite, alkaline earth fluorides, calcium phosphates and hydroxyapatite.

3. The composite filler of claim 2, wherein the at least one particle comprises at least one oxide selected from the group consisting of alumina, zinc oxide, titania, zirconia, yttria and rare earth oxides.

4. The composite filler of claim 2, wherein the at least one particle comprises at least one oxide and a non-oxide filler selected from hydroxyapatite, fluoroapatite and alkaline earth fluorides.

5. The composite filler of claim 1, wherein the porous inorganic particles comprises at least one oxide selected from zirconia, yttria and rare earth oxides at a concentration greater than 25% by weight of the porous inorganic particles.

6. The composite filler of claim 1, wherein the composite filler is at least 84 percent by weight porous inorganic particles and wherein the average particle diameter of the composite filler is not more than 2-times the average particle diameter of the porous inorganic particles.

7. The composite filler of claim 1, wherein the difference between the refractive indices of the polymer and the porous inorganic particles is greater than 0.03.

8. The composite filler of claim 1, wherein the difference between the refractive indices of the polymer and the porous inorganic particles is greater than 0.06.

9. The composite filler of claim 1, wherein the Transparency Index of the composite filler is greater than 8.

10. The composite filler of claim 1, wherein the visible light transmission of a one centimeter thickness is greater than 25.0%, when the composite filler is dispersed into a fluid of substantially the same refractive index at a volume fraction of at least 25%.

11. The composite filler of claim 1, wherein the visible light transmission of a one centimeter thickness is greater than 50.0%, when the composite filler is dispersed into a fluid of substantially the same refractive index at a volume fraction of at least 25%.

12. The composite filler of claim 1, wherein the refractive index is between 1.48 and 1.58.

13. The composite filler of claim 1, wherein the refractive index is between 1.52 and 1.58.

14. The composite filler of claim 1, wherein the difference between the measured refractive index of the composite filler does not differ by more than 0.01 from the calculated volume average index of the composite filler.

15. The composite filler of claim 1, wherein the composite filler has a mean particle diameter of from 3 to 20 microns.

16. The composite filler of claim 1, wherein the composite filler has a mean particle diameter of from 4 to 10 microns.

17. The composite filler of claim 1, wherein the porous inorganic particles are sintered porous inorganic particles.

18. The composite filler of claim 1, wherein the composite filler is a dental composite filler.

19. The composite filler of claim 1 dispersed in a light polymerizable resin.

20. The composite filler of claim 19, wherein the refractive index of the light polymerizable resin is essentially the same as the refractive index of the composite filler.

* * * * *